(12) United States Patent
Su et al.

(10) Patent No.: US 9,168,159 B2
(45) Date of Patent: Oct. 27, 2015

(54) SURFACE TEXTURED IMPLANTS

(75) Inventors: Shih-Horng Su, Irvine, CA (US);
Fuh-Sheng Chen, San Diego, CA (US);
Debashis Dutta, Irvine, CA (US)

(73) Assignee: Biosensors International Group, Ltd., Hamilton (BM)

( * ) Notice: Subject to any disclaimer, the term of this patent is extended or adjusted under 35 U.S.C. 154(b) by 53 days.

(21) Appl. No.: 13/128,078

(22) PCT Filed: Nov. 4, 2009

(86) PCT No.: PCT/US2009/063277
§ 371 (c)(1),
(2), (4) Date: Nov. 8, 2011

(87) PCT Pub. No.: WO2010/053991
PCT Pub. Date: May 14, 2010

(65) Prior Publication Data
US 2012/0046736 A1  Feb. 23, 2012

Related U.S. Application Data

(60) Provisional application No. 61/111,833, filed on Nov. 6, 2008.

(51) Int. Cl.
| | |
|---|---|
| *A61F 2/06* | (2013.01) |
| *A61F 2/82* | (2013.01) |
| *A61F 2/00* | (2006.01) |
| *A61K 33/00* | (2006.01) |
| *A61F 2/04* | (2013.01) |
| *A61F 2/848* | (2013.01) |

(52) U.S. Cl.
CPC .............. *A61F 2/82* (2013.01); *A61F 2/0077* (2013.01); *A61F 2/04* (2013.01); *A61F 2/06* (2013.01); *A61F 2/848* (2013.01); *A61F 2002/0081* (2013.01); *A61F 2230/0002* (2013.01); *A61F 2250/0067* (2013.01); *A61F 2250/0071* (2013.01); *A61K 33/00* (2013.01); *A61L 2400/12* (2013.01)

(58) Field of Classification Search
CPC .................................................. A61L 2400/12
USPC ........................................................ 623/1.46
See application file for complete search history.

(56) References Cited

U.S. PATENT DOCUMENTS

| | | | |
|---|---|---|---|
| 6,805,898 B1 * | 10/2004 | Wu et al. ...................... 427/2.25 |
| 2006/0212109 A1 | 9/2006 | Sirhan et al. | |
| 2007/0282432 A1 | 12/2007 | Stinson et al. | |
| 2007/0286941 A1 | 12/2007 | Huang et al. | |
| 2008/0206441 A1 | 8/2008 | Krivoruchko | |
| 2008/0215141 A1 | 9/2008 | Hossainy | |
| 2009/0076591 A1 | 3/2009 | Girton et al. | |
| 2009/0112310 A1 | 4/2009 | Zhang | |

OTHER PUBLICATIONS

International Search Report dated Dec. 24, 2009, issued in International Patent Application No. PCT/US09/63277, filed Nov. 4, 2009.

(Continued)

*Primary Examiner* — Jacqueline Woznicki
(74) *Attorney, Agent, or Firm* — Kilpatrick Townsend & Stockton LLP

(57) ABSTRACT

Devices and methods for controlling the flaking of coating fragments from medical implants and improving the delivery of therapeutic agents from such coatings are described.

11 Claims, 11 Drawing Sheets

(56) References Cited

OTHER PUBLICATIONS

Extended European Search Report from EP Appl. No. 09825359.4, dated Dec. 10, 2012.

* cited by examiner

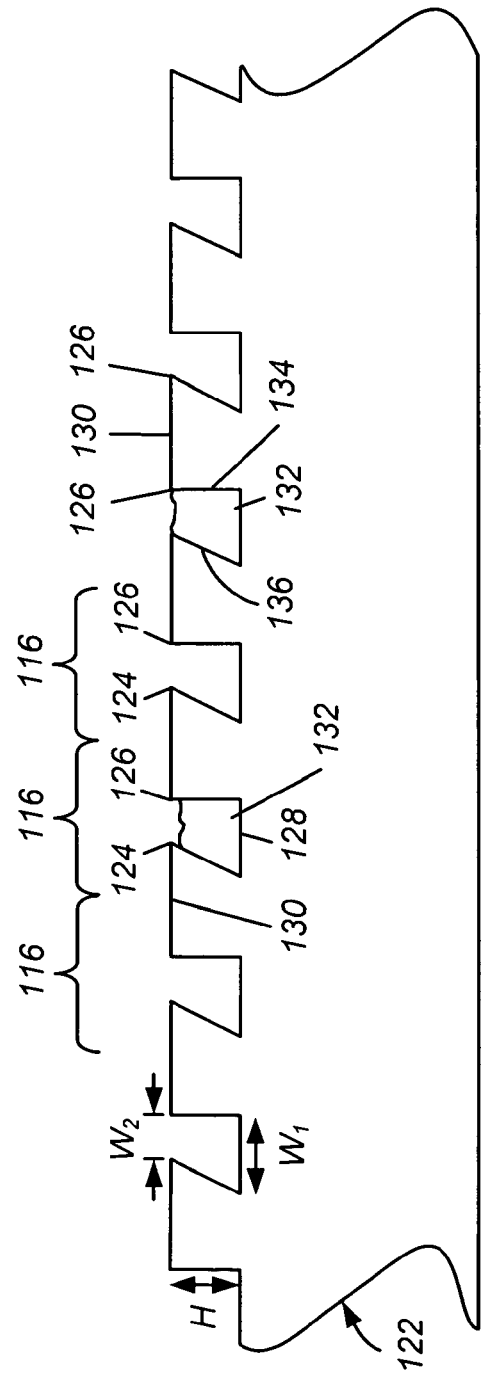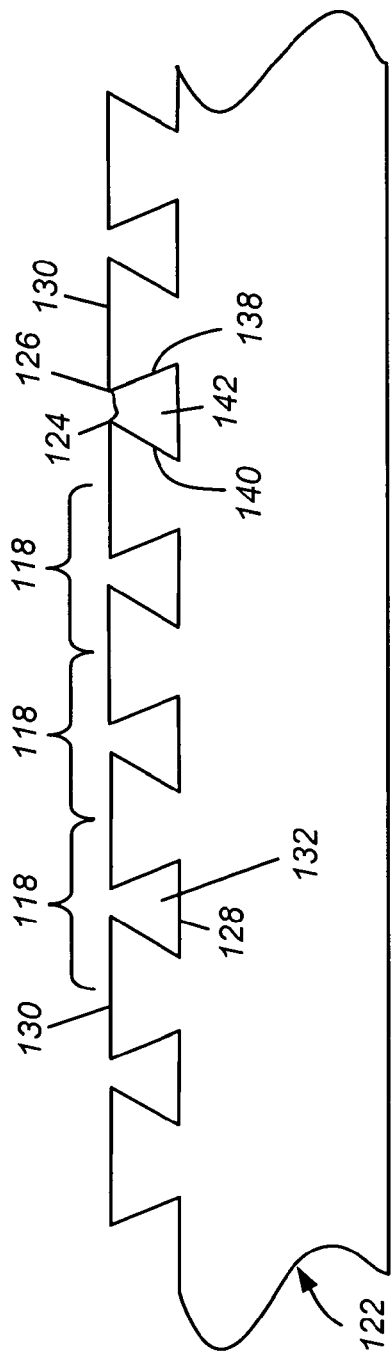
FIG. 8A
FIG. 8B

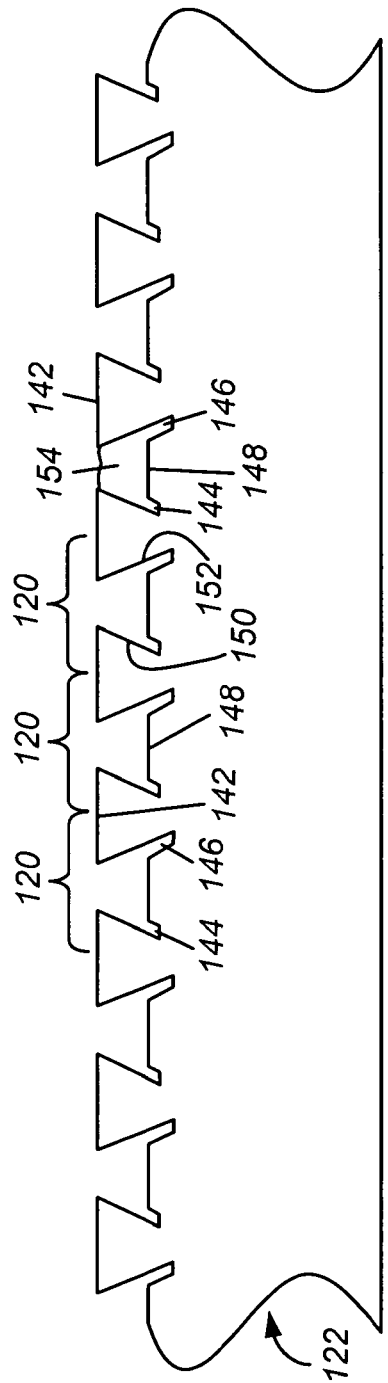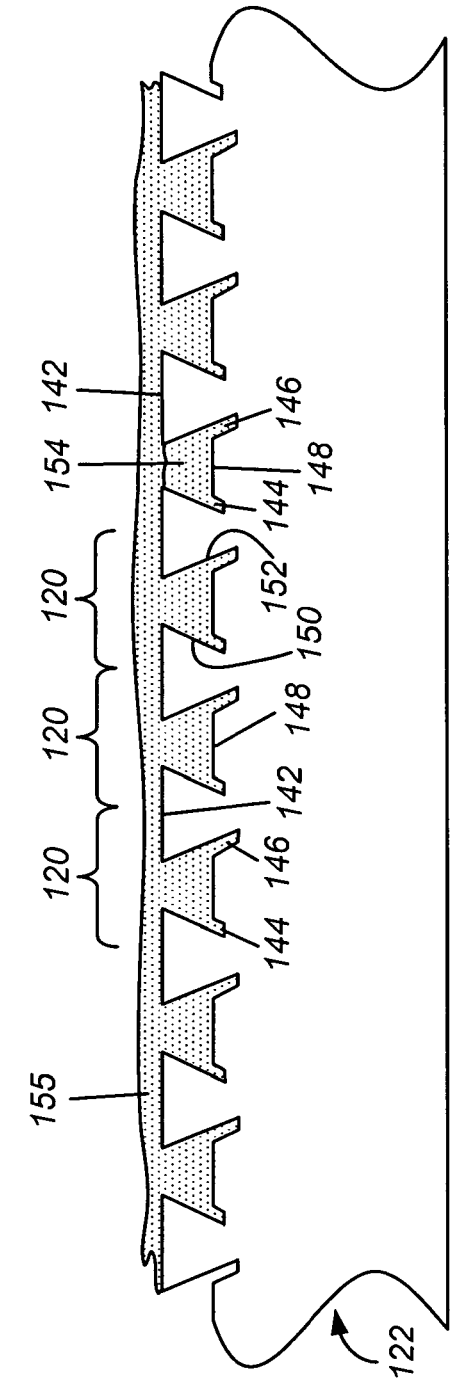

SURFACE TEXTURED IMPLANTS

CROSS-REFERENCES TO RELATED APPLICATIONS

This application is the U.S. National Stage entry of International Application No. PCT/US2009/063277, filed Nov. 4, 2009, which claims benefit of priority to U.S. Provisional Patent Application No. 61/111,833, filed Nov. 6, 2008, entitled "Surface Textured Implants," which are incorporated herein by reference for all purposes.

The following references and additional references cited, herein, are hereby incorporated by reference in their entirety.
U.S. Pat. No. 6,805,898
U.S. Pat. No. 6,800,089
U.S. Pat. No. 6,913,617
U.S. Pat. No. 7,335,314
U.S. Pat. No. 6,764,505
U.S. Patent Publication No. 20080097591
U.S. Patent Publication No. 20080097568
U.S. Patent Publication No. 20050211680
International Patent Pub. No. WO/2008/027872
Stout, K. J. et al. (1994) *The development of methods for the characterization of roughness on three dimensions*, Publication No. EUR 15178 EN of the Commission of the European Communities, Luxembourg.
Barbato, G. et al. (1995) *Scanning tunneling microscopy methods for roughness and micro hardness measurements*, Synthesis report for research contract with the European Union under its programme for applied metrology, European Commission Catalogue number: CD-NA-16145 EN-C, Brussels Luxemburg. 109 pages.
Jørgensen, K. et al. (1993) The Scanning Tunneling Microscope and Surface Characterisation, *Nanotechnology* 4:152-158.

TECHNICAL FIELD

The present devices and methods are in the field of implantable devices or prostheses, particularly devices that include a therapeutic surface coating.

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Drug-eluting stents are commonly used in coronary angioplasty procedures, after a diseased vessel has been opened by balloon angioplasty, to maintain the opened diameter of the vessel and to reduce the risk that the vessel will re-narrow by a process known as restenosis. Stents of this type are typically composed of a radially expandable stent body, e.g., a metal stent body, whose outer surface is coated with a drug-containing polymer coating from which the anti-restenosis drug is eluted over a period of a few week to several months. The stent is carried to the target vascular site in a contracted condition on the catheter balloon. As the balloon is expanded to open a narrowed portion of a vessel, the stent carried on the balloon is expanded against the vessel wall for deployment in the vessel. During this stent expansion, the stent coating is exposed to radial stresses and may fracture, releasing flaked coating material into the bloodstream. Flaked pieces of sufficient size can serve as sites for blood clotting, posing a concern for embolism.

Previous efforts to address this problem have involved increasing the adhesion of the coating to the implant, in an effort to minimize flaking. One way to increase adhesion is to roughen or texture the surface of the implant, as described in U.S. Pat. Nos. 6,805,898 and 7,335,314 (Wu et al.), U.S. Pat. No. 6,913,617 (Reiss), and WO 08/027,872. However, when medical implants experience sufficient structural deformation, rigid and semi-rigid coatings inevitably crack and flake off in fragments, fibers, or strands, risking clinical complications such as embolism, blood flow interruption/disruption, and blood clots. This problem is observed, for example, in the case of coated filaments of vascular stents, which are typically expanded following delivery to a preselected site of implantation. A related problem is observed when two stents are implanted in an overlapping or juxtaposed configuration, wherein contact between the stents causes damage to the coating of one or both stents.

It is, therefore, apparent that simply increasing the adhesion of the coating to the surface of the medical implant does not fully address the problems of flaking, dislodgement and coating embolization.

BRIEF SUMMARY OF THE INVENTION

The following aspects and embodiments thereof described and illustrated below are meant to be exemplary and illustrative, not limiting in scope.

In one aspect, the invention provides a radially expandable device for introducing into the body of a subject to produce a beneficial effect. The device comprises a coating and an upper surface that contacts tissue at a treatment site. The upper surface comprises one or more texture features designed to interact with the coating and cause fragments of the coating to flake off the upper surface as a result of radial expansion of the device at the treatment site. The resulting fragments are too small to cause thrombi and/or emboli.

The texture features of the device of the present invention control the size of the coating fragments. Further, the texture features of the device control the shape of the fragments. In addition, texture features also control the quantity of the fragments.

In one embodiment, the texture features of the present invention comprise one or more peaks, and/or one or more valleys and/or one or more plateaus. Further, the peaks comprise stress risers that control the initiation and propagation of stress fractures in the coating.

These and other objects and features of the invention are made more fully apparent in the following detailed description of the invention.

BRIEF DESCRIPTION OF THE DRAWINGS

FIGS. 8A-8D show texture features that include elevated plateaus between peaks, of peaks and valleys.

DETAILED DESCRIPTION OF THE INVENTION

Figure 1A:
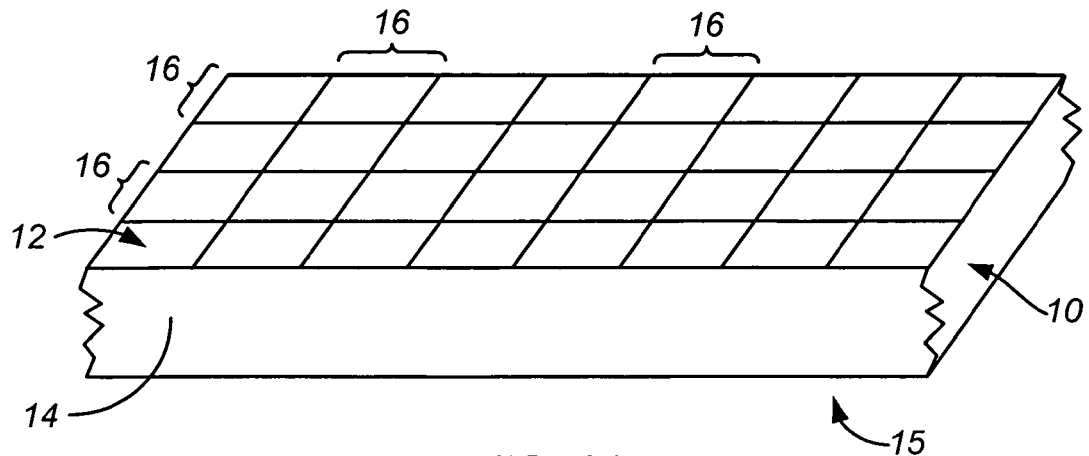
FIGS. 1A and 1B show exemplary textured surfaces on a filament.

Before the inventive devices and methods are disclosed and described, it is to be understood that this invention is not limited to stents, or the like, as such may vary. It is also to be understood that the terminology used herein is for the purpose of describing particular embodiments only and is not intended to be limiting.

The present devices and methods relate to a vascular implant, such as a stent, having a surface texture that controls the size and shape of fragments of coating material that may separate from the implant, and methods for manufacturing such devices. The devices and methods are particularly useful for controlling the size and shape of coating fragments that originate from rigid and semi-rigid coatings, which have the greatest tendency to break and flake off the surface of a medical implant following structural deformation.

The devices and methods may best be understood with reference to the accompanying drawings. Similar features are identified using the same reference numerals.

DEFINITIONS

As used herein, the term "medical implant" or "implant" refers to a stent, pin, screw, plate, mesh structure, orthopedic appliance, RFID tag, pacemaker, gastric band/collar, cosmetic implant, or other devices suitable for implantation into the body of a mammalian subject. An exemplary implant is an expandable vascular stent.

As used herein, a "texture feature" or "texture element" is a discrete surface region within a surface texture that can be defined in terms of shape, volume, area and/or dimensions.

As used herein, the term "valley" refers to a depression, indentation, trough or characteristic extending toward a device's lower surface that forms a portion of a texture feature.

As used herein, the term "peak" refers to a protrusion, projection, elevation or characteristic extending toward a device's upper surface that forms a portion of a texture feature.

As used herein, the term "comparatively non-textured," as it applies to the region for attachment of coating to the surface of a medical implant, refers to a texture feature having less than 20%, and preferably less than 10%, of the valley to peak height of a textured region.

As used herein, the term "flake" or "flake off" refers to the detachment, release or separation of a portion (i.e., a fragment) of coating from the surface of a medical implant in response, for example, to structural deformation or handling. Depending on the particular medical implant and coating concerned, such flaking off may be relied upon to produce an intended therapeutic effect, or may be an unintended or unavoidable consequence of the use of a particular coating material with a particular medical implant.

As used herein, the terms "break," "crack" and "fracture" are intended to refer to the process by which stress fractures initiate and/or propagate in a rigid or semi-rigid coating of a medical implant subjected to structural deformation or handling. Breaks and cracks may be encouraged at a preselected location in a coating by the use of stress risers.

As used herein, a "stress riser" is a feature associated with the surface of a coated medical implant that concentrates the stress of structural deformation at a particular location in the coating, thereby causing breaks or cracks to initiate at, and propagate from, that location.

As used herein, the term "structural deformation" refers to distortion, bending, stretching, flexing or other physical changes to the surface of a medical implant that can cause at least a portion of a rigid or semi-rigid coating to separate from the surface.

As used herein, the term "rigid or semi-rigid," as it refers to coatings, is intended to broadly encompass coatings that are relatively non-elastic, and which therefore may fracture and flake during structural deformation, as when a coated stent is radially expanded or deformed along its radial or longitudinal axis during deployment.

Surface Textured Implants

A first aspect of the present invention is a surface textured implant for introducing into the body of a subject to produce a beneficial effect. In one embodiment, the implant is a stent having a body formed of expandable, interconnected elements, such as metal or polymer wires or filaments, according to well-known construction of radially expandable stents. Such stents are formed, for example, by laser cutting a cylindrical metal or polymer tube. In the figures described below, the structures shown are intended to represent portions of individual filaments or elements making up the stent. Such a filament structure has an upper surface that is in contact with the vessel wall when the stent is deployed, side surfaces, and a lower surface that forms part of the interior surface of the stent in the deployed condition. It will be understood that the structures may also illustrate other surface elements of implants.

With this background in mind, FIG. 1A shows a portion of a stent filament 10 which, together with other interconnected filaments, makes up the body of a stent. The filament has a first, upper surface 12 forming part of the outer surface of a stent, a second lower surface 15 (dotted arrow) that forms part of the inner surface of the stent, and one or more side surfaces 14. As noted, where the implant is a vascular stent, the second surface may be in contact with blood present in the lumen of a blood vessel.

Figure 1B:
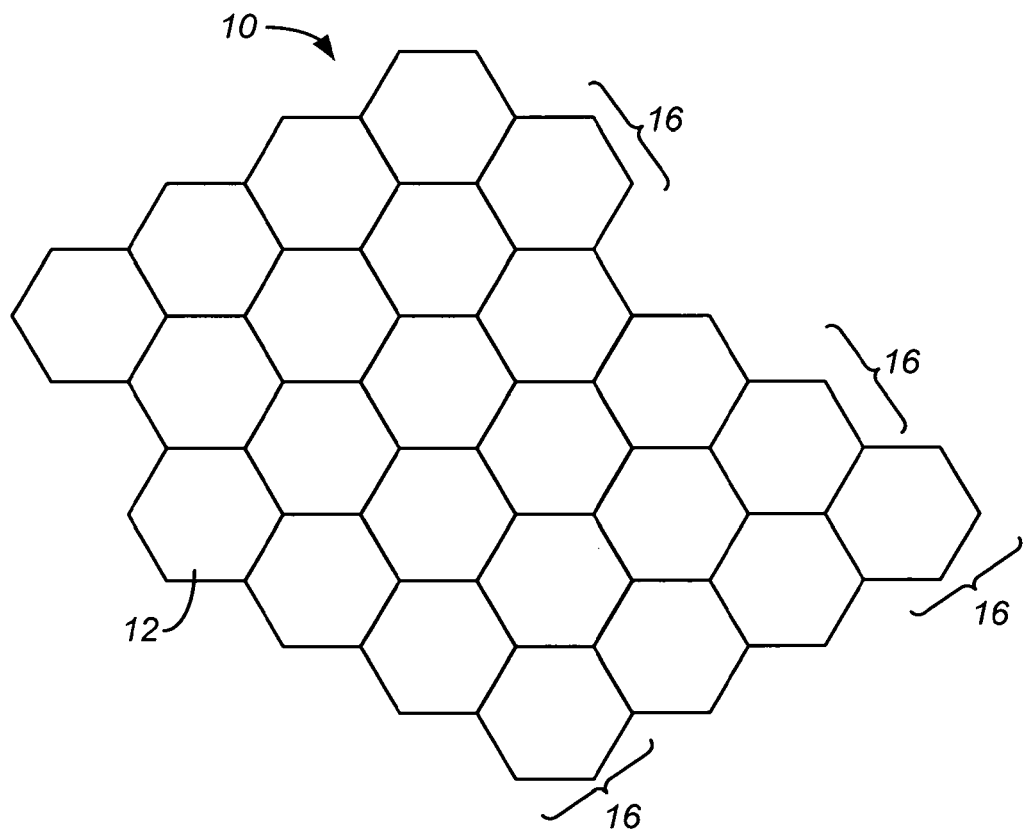

The first surface 12 of filament 10 has a texture that includes one or more discrete texture features 16 designed to interact with a coating (shown in subsequent figures) applied to the filament. These texture features may cover all or only a portion of the filament surface and may be arranged in the form of a grid (FIG. 1A), honeycomb pattern (FIG. 1B) or other configuration that preferably allows the texture features 16 to be grouped together at high density on an upper surface 12 of a filament 10. Exemplary regular shapes for texture features include, but are not limited to, rectangles, hexagons, geometric shapes, fishscales, archimedes, diamonds, cross-hatching, mathematically modeled shapes and the like. Irregular shapes for texture features, including but not limited to shapes which can not be defined or represented by mathematics, are also used with the present invention. Additional texture features are further described, below. For convenience, similar features are identified using the same reference numerals.

Texture Features with Peaks or Valleys to Control Flaking

Figure 2A:
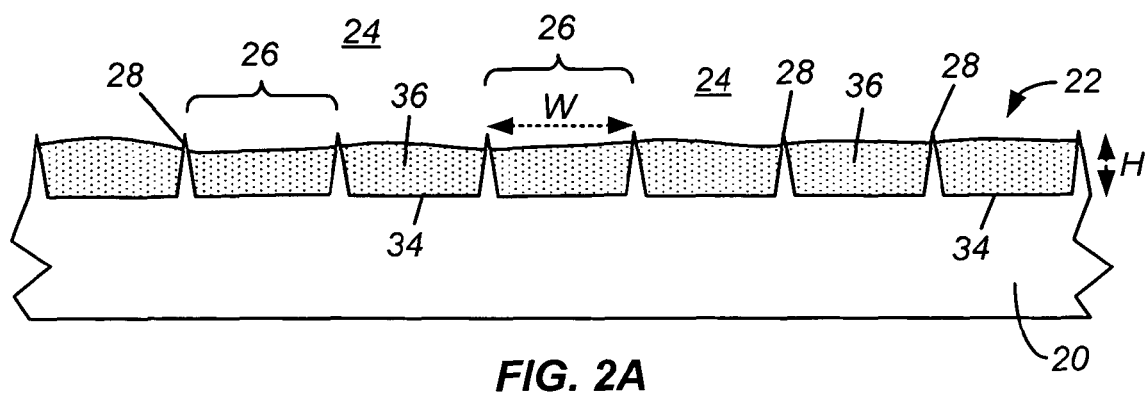
FIG. 2A shows exemplary texture features having peaks protruding above a coating.
Figure 3A:
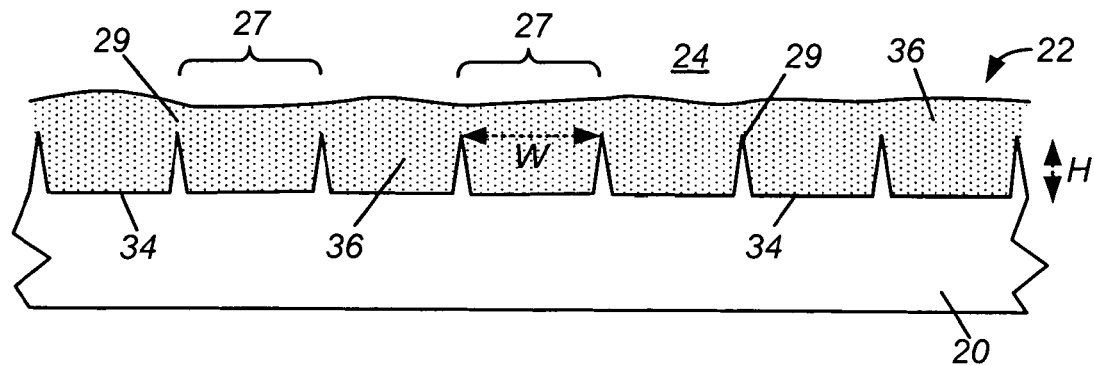
FIG. 3A shows exemplary texture features wherein a coating covers peaks.
Figure 4A:
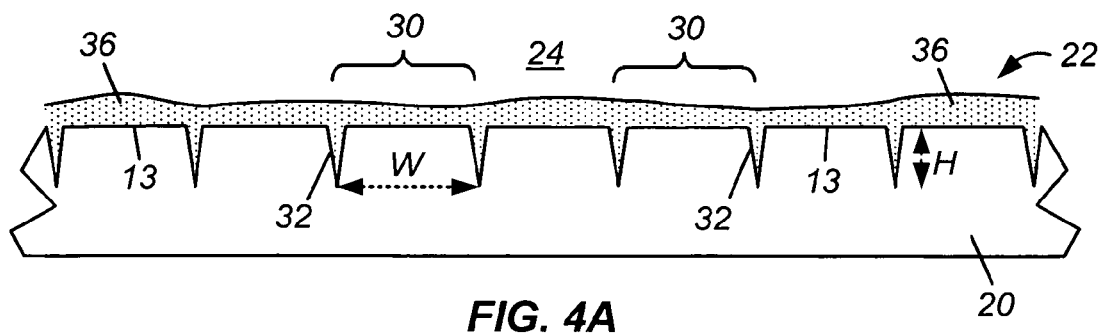
FIG. 4A shows exemplary texture features wherein a coating covers valleys.

FIGS. 2A, 3A and 4A show cross-sectional side views of several embodiments of texture features that include peaks and/or valleys. In all these figures, an upper surface 22 of a filament 20 is in contact with a body tissue 24, generally represented by the area above the diagrams. In FIGS. 2A and 3A, discrete texture features 26, 27 having a width (W) are defined by peaks 28, 29 which protrude from the upper surface of the filament. In FIG. 4A, texture features 30 having a width (W) are defined by valleys 32 in the surface of the filament. Where the texture feature has an irregular shape, the width (W) is defined as the widest dimension between peaks or valleys. In both cases, the texture features may further include a plateau region 34 between the peaks or valleys, as appropriate. The plateau region may be substantially non-textured or may have an additional texture to increase adhesion of a coating 36, which is further illustrated in the figures.

As illustrated in FIGS. 2A, 3A and 4A, the height of the peaks or depth of the valleys further defines height (H) of the texture feature. Since a texture feature may be bounded by the surface of the filament (i.e., the plateau) and peripheral peaks or valleys, and is only required to be open to the body tissue that it contacts once implanted, the texture feature also defines a volume (V), some or all of which can be filled with coating material.

Where texture features 26, 27 are defined by peaks 28, at least a portion of one or more peaks may protrude above the coating (FIG. 2A) or be covered by the coating (FIG. 3A). Where texture features 30 are defined by valleys 32, the coating may initially cover the valleys (FIG. 4A).

Texture features defined by peaks and valleys provide several advantages in terms of coating adhesion and flaking control. First, the texture features may increase the adhesion of the coating to the surface of the implant, thereby reducing flaking of the coating in response to surface deformation. Second, the texture features may introduce stress risers on the surface of the implant, such that if or when the amount of structural deformation to the implant surface becomes sufficient to overcome the adhesion of at least a portion of the coating to the surface of the implant, the texture features control the size, shape and quantity of coating fragments that flake off the surface of the implant. Such surface distortion commonly occurs as a result of radial expansion of a vascular stent at the site of implantation.

Figure 2B:
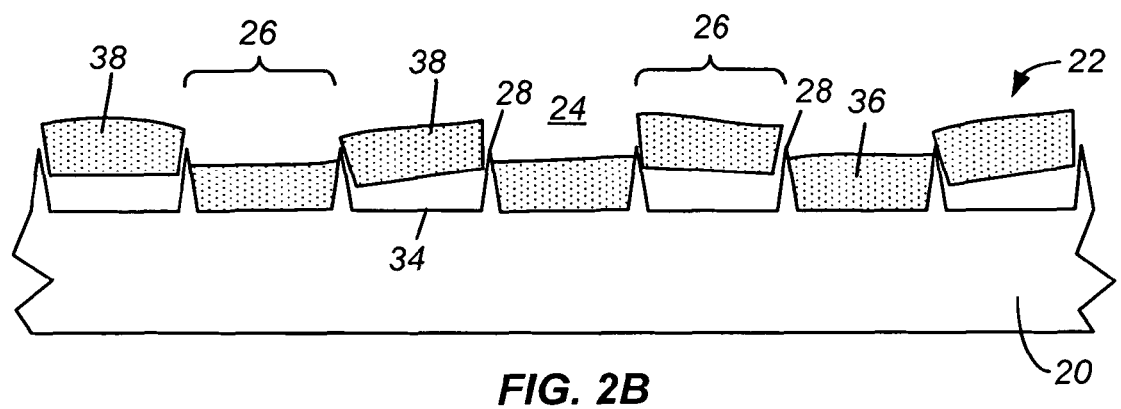
FIG. 2B shows the detachment of coating fragments in response to surface deformation.
Figure 3B:
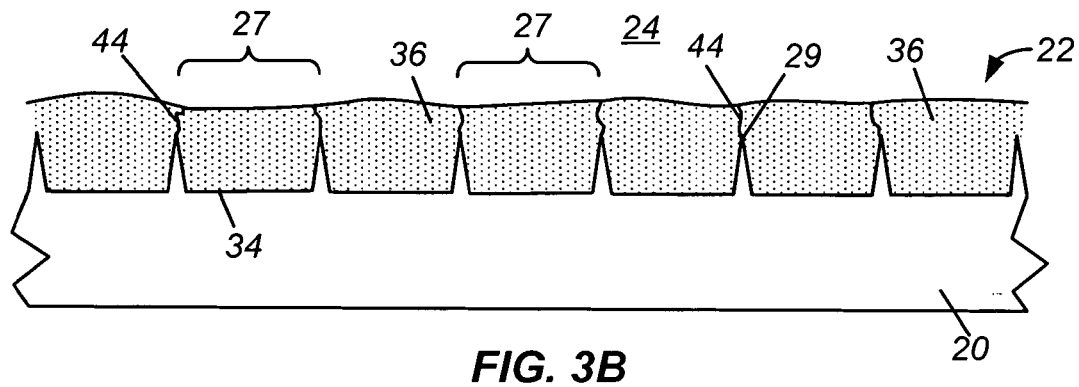
FIG. 3B shows stress fractures that occur in response to surface deformation.
Figure 3C:
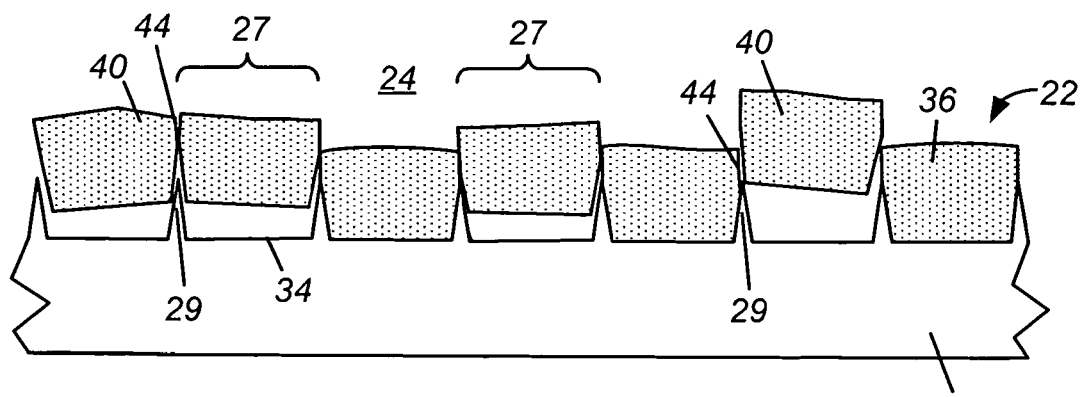
FIG. 3C shows the detachment of coating fragments in response to surface deformation.
Figure 4B:
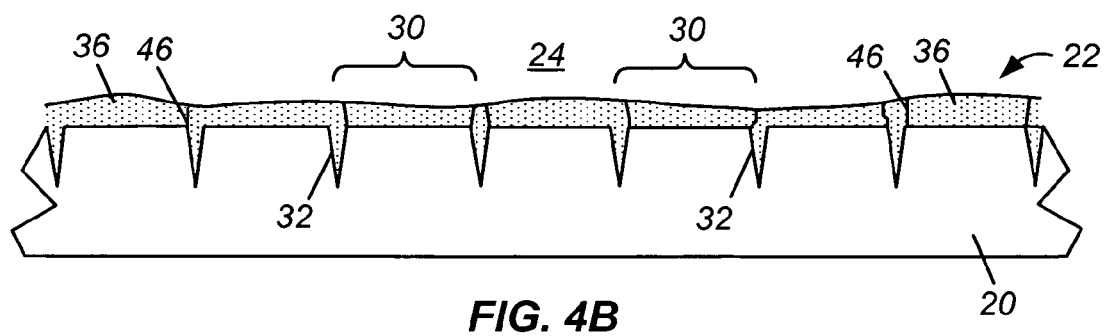
FIG. 4B shows stress fractures that occur in response to surface deformation.
Figure 4C:
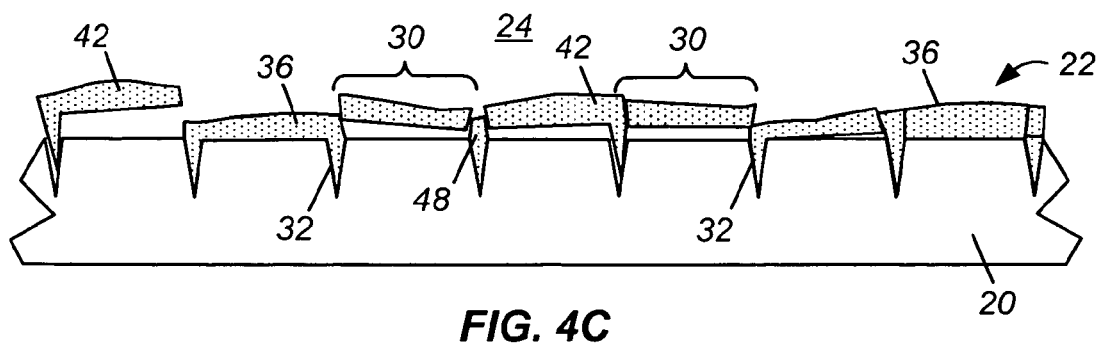
FIG. 4C shows the detachment of coating fragments in response to surface deformation.

The manner in which texture features control the size, shape and quantity of coating fragments is illustrated in subsequent figures, wherein similar structures are represented by the same reference numerals used above. Where texture features 26 are defined by peaks 28 that protrude above a coating 36, as shown in FIG. 2A, the size, shape and quantity of released coating fragments 38 are predetermined by the dimensions of the texture features, as shown in FIG. 2B. Where texture features 27 are defined by peaks 29 that are covered by a coating 36, as shown in FIG. 3A, the peaks function as stress risers to control the initiation and propagation of stress fractures 44 in the coating (FIG. 3B), which direct the flaking of coating fragments 40 along the stress fractures 44 originating from the peaks (FIG. 3C).

Where texture features 30 are defined by valleys 32, as shown in FIG. 4A, the valleys function as stress risers to control the initiation and propagation of stress fractures 46 in the coating (FIG. 4B), which direct the flaking of coating fragments 42 along the stress fractures (FIG. 4C). The coating may detach so as to leave a small portion of the coating 48 in the valleys or detach completely thereby including the portion of coating in the valleys.

Texture Features with Peaks and Valleys to Control Flaking

Figure 5A:
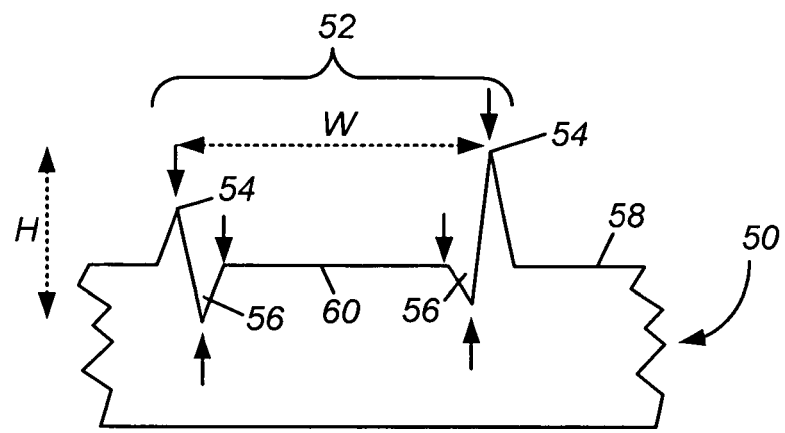
FIGS. 5A-5D show an exemplary texture feature having both peaks and valleys.

A particular type of texture feature for use in controlling coating flaking includes both peaks and valleys. As illustrated in FIG. 5A, such a texture feature 52 is defined by peaks 54 that flank valleys 56 in a first surface 58 of a filament 50. These peaks and valleys serve as stress risers (dotted arrows) to control coating flaking. As before, the texture feature includes a plateau 60, which may be comparatively non-textured or may include an additional texture to increase adhesion of a coating. Each texture feature can be described by a width (W), measured between the peaks, and a height (H), measured between the tops of the peaks and bottom of the valleys. As above, the first surface of the filament may have one or a plurality of adjacent texture features on a portion of the first surface or, alternatively, the first surface may be substantially or completely covered by such features.

Figure 5B:
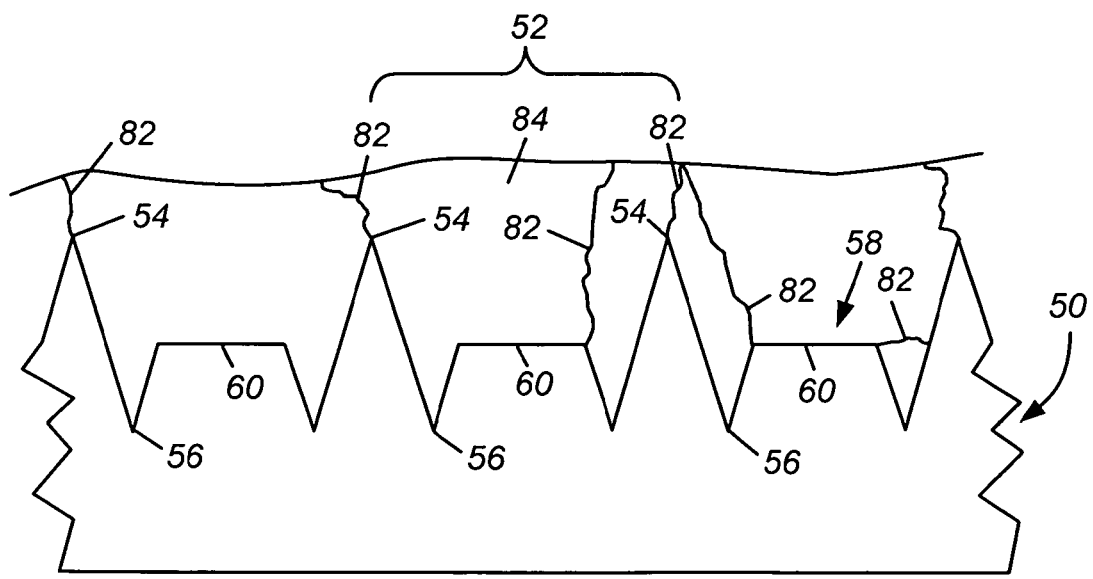
Figure 5C:
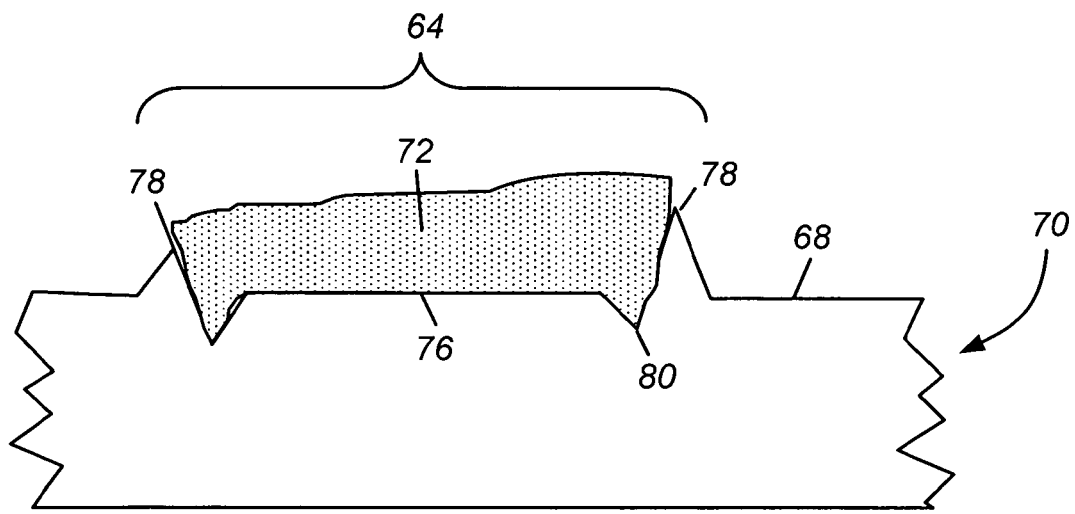
Figure 5D:
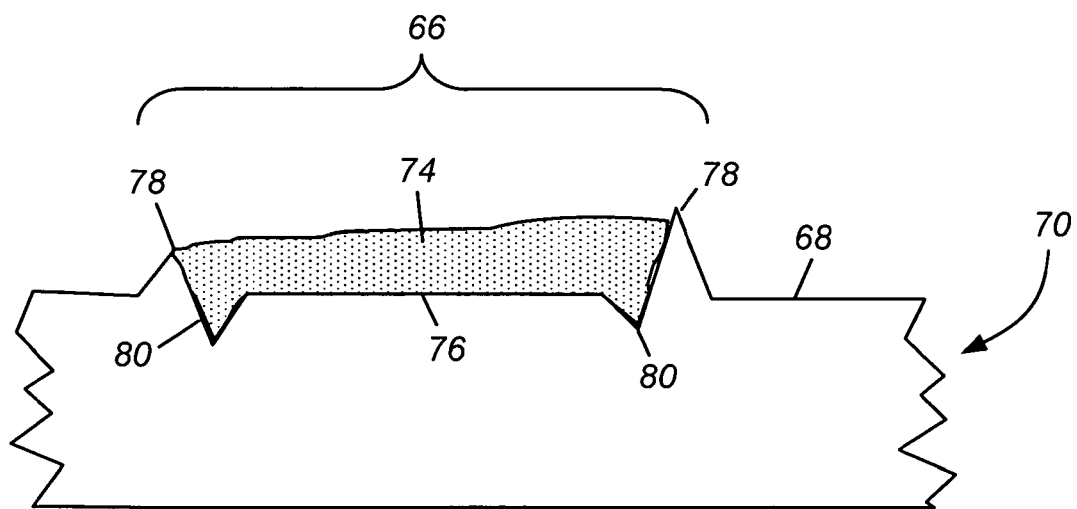

FIGS. 5C and 5D illustrate texture features 64, 66 on a first surface 68 of a filament 70, following application of a rigid or semi-rigid coating 72, 74. The coating contacts a plateau 76 between peaks 78 and valleys 80, fills or partially fills the valleys, and contacts at least a portion of the inside surfaces of the peaks. The thickness of the coating may be such that the peaks are covered by the coating, as shown in FIG. 5C, or at least a portion of one or more of the peaks protrude above the coating, as shown in FIG. 5D. While isolated texture features 52, 64, 66 are illustrated in FIGS. 5A and 5C, it will be apparent that the surface of a filament may have a plurality of texture features, as shown in the previous figures.

Using the same reference numerals as used in FIG. 5A to indicate similar features, FIG. 5B illustrates the initiation and propagation of stress fractures 82 in a coating 84, as a consequence of the numerous stress risers introduced by a peak-and-valley type of texture feature 52.

Figure 6A:
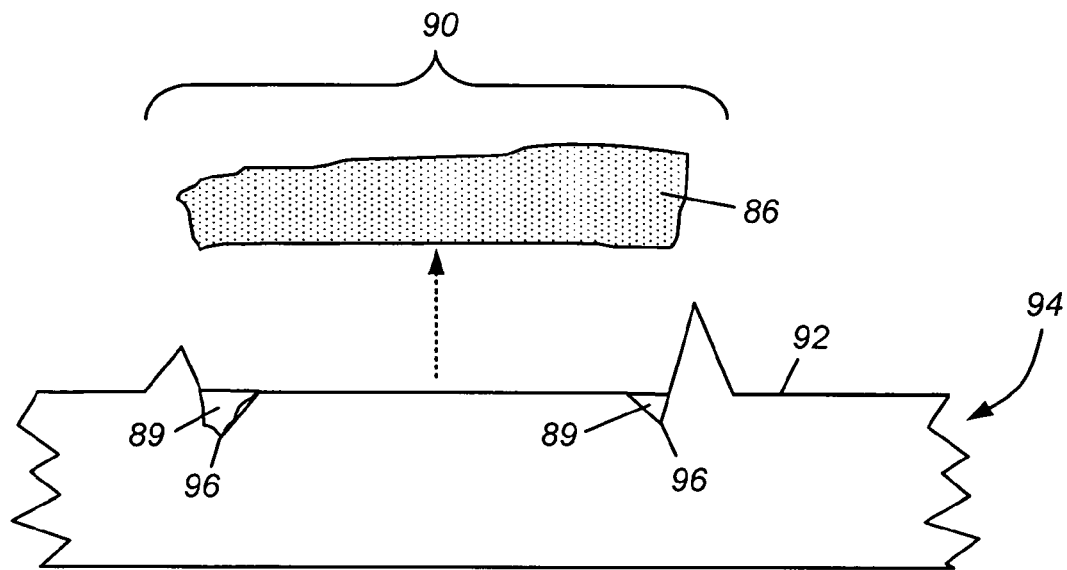
FIGS. 6A and 6B show detachment of coating fragments from a peak-and-valley texture feature in response to surface deformation.
Figure 6B:
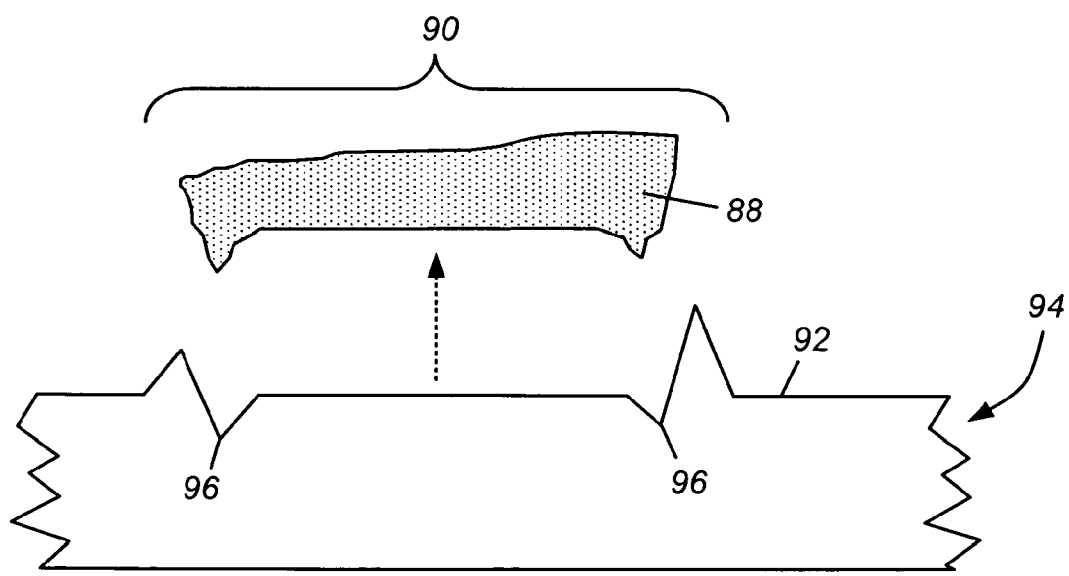

FIGS. 6A and 6B illustrate embodiments by which a fragment of coating 86, 88 having a predetermined size and shape may detach from a peak-and-valley type of texture feature 90, as generally illustrated in FIG. 5A. It is to be understood that additional embodiments by which a coating fragment may detach from a texture feature not specifically illustrated herein are also included within the scope of the present invention. Release occurs when structural deformation of a first surface 92 of a filament 94 produces sufficient stress on the coating to overcome adhesion to the surface 92. The coating may detach so as to leave a relatively small portion of the coating 89 in all or a portion of one or more valleys 96 of the texture feature (an example, of which, is shown in FIG. 6A), or detach completely (as shown in FIG. 6B). The amount of coating, if any, that remains in the valleys is relatively small compared to the amount of coating that flakes off.

Figure 7A:
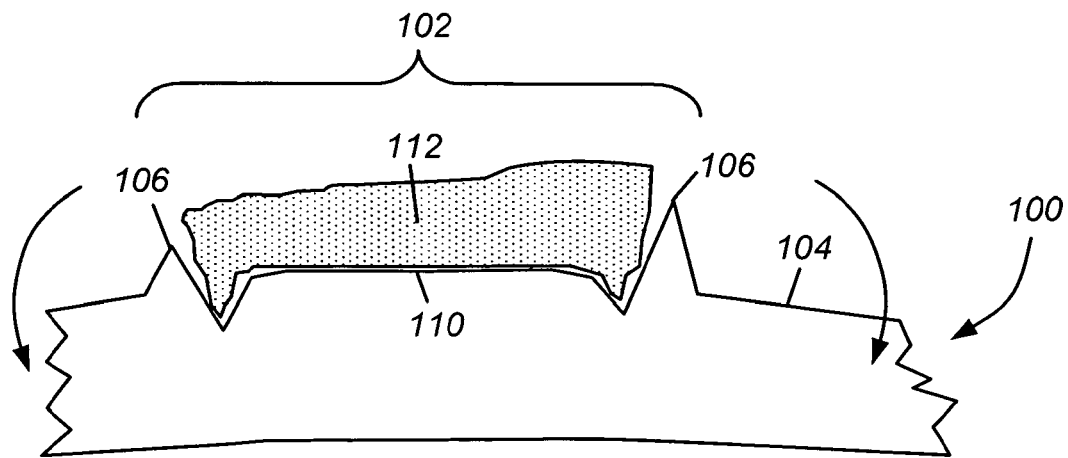
FIGS. 7A and 7B show the response of coating fragments attached to a peak-and-valley texture feature in response to surface deformation.
Figure 7B:
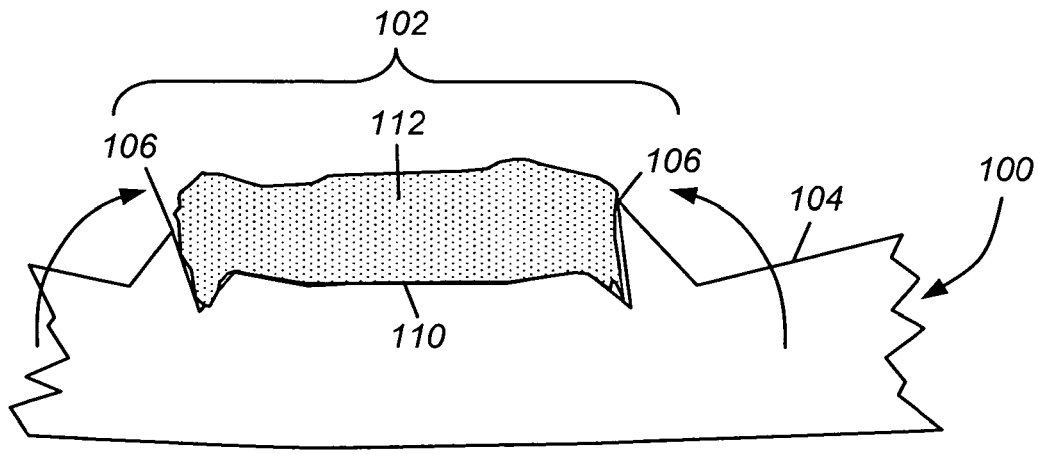

FIGS. 7A and 7B further illustrate embodiments of the interactions between the coating 112 and the peak-and-valley-texture features 102 in response to particular forms of stress produced by deformation of a first surface 104 of a filament 100. In FIG. 7A, the ends of the filament are drawn in a downward direction, indicated by the arrows, pulling peaks 106 of the texture feature away from the coating 112. As stress increases, the coating becomes attached only to a plateau 110 portion of the texture feature, and eventually detaches as shown in FIGS. 6A and 6B. This type of surface deformation, and the resulting stresses caused by the deformation, can be found, for example, at the surface of a stent following insertion into a blood vessel and subsequent radial expansion at a vascular site.

In FIG. 7B, the ends of the filament 100 are drawn in an upward direction, indicated by the arrows, pushing the peaks of the texture feature toward (i.e., into) the coating 112. As the amount of deformation at the first surface 104 of the filament increases, the coating 112 may initially be clamped and retained by the inwardly drawn peaks 106. However, as deformation increases, the space (i.e., volume) defined by the texture feature becomes insufficient to contain the amount of coating originally applied to the surface of the filament, and a fragment of the coating eventually detaches, as shown in FIGS. 6A and 6B. This type of surface deformation, and the resulting stresses caused by the deformation, can be found, for example, in the struts or ductile hinges of a stent following insertion into a blood vessel and subsequent radial expansion at a vascular site.

Texture Features with Elevated Plateau Regions

A further variation of the present texture features provides a cross-sectional shape suitable for holding captive regions of coating to further reduce flaking and detachment. Exemplary texture features are illustrated in FIGS. 8A-8D. As illustrated in previous drawings, the texture features 116, 118, 120 are shown arranged on the surface of a vascular stent filament 122. As before, the texture features include peaks or peaks and valleys flanking a lower plateau region. However, the embodiments illustrated in FIGS. 8A-8D include peaks or peaks and valleys flanking a lower plateau region and further being connected through an additional elevated plateau region.

For example, FIG. 8A shows texture features 116 having peaks 124, 126 of height H flanking lower plateau regions 128, which peaks are further connected through elevated plateau regions 130. The resulting texture features have a cross-section that is wider at the level of the lower plateau region 128 (i.e., $W_1$) than at the level of the elevated/upper plateau region 130 (i.e., $W_2$), such that portions of coating 132 (shown filing at least a portion of one or more of the texture features) are held in place and cannot readily detach from the texture features.

The embodiment shown in FIG. 8B is similar to that shown in FIG. 8A, except that the cross-section of the texture features have a different shape. For example, in FIG. 8A, one side 134 of the texture features is substantially vertical and the other side 136 is angled inwardly toward a portion of the coating 142. In contrast, as shown in FIG. 8B, both sides 138, 140 of the texture features 118 are angled inwardly toward a portion of the coating. Note that features common to FIGS. 8A and 8B are identified using the same reference numerals.

FIG. 8C shows a texture feature having an elevated plateau region 142, similar to that shown in FIGS. 8A and 8B, but further including valleys 144, 146 flanking a lower plateau region 148, as described with reference to FIGS. 5A-7B. At least one side and optionally both sides 150, 152 of the texture features may be angled inwardly toward a portion of the coating 154 as shown in FIGS. 8A and 8B, respectively. Further, one side may also be vertical, as shown in FIG. 8A.

Where a texture feature includes elevated plateau regions, at least a portion of the coating may be below the level of the elevated plateaus, as shown in FIGS. 8A-C, or above the level of the elevated plateaus, as shown in FIG. 8D. Note that the same reference numerals are used in FIGS. 8C and 8D, except that in FIG. 8D the layer of coating 155 above the elevated plateaus 142 is separately indicated. Flaking is maximally reduced where the level of the coating is below the level of the elevated plateaus; however, contact between a body tissue, such as a vascular wall, is maximized when the level of the coating is above the level of the elevated plateaus. Note that the portion of the coating above the elevated plateaus is still subject to controlled flaking as a result of the stress fractures that can propagate through the coating from the various stress risers introduced by the texture features (see, e.g., FIG. 5B).

Design of Texture Features

The texture features are designed to retain the coating when the surface of the implant is not experiencing structural deformation and release fragments of coating having a controlled size and shape when the surface of the implant experiences sufficient structural deformation to overcome the adhesion between the coating and the textured surface of the implant. In particular, structural deformation at the surface of the implant causes fracture lines to promulgate at the site of the stress risers created by the peaks and/or valleys in the texture feature, directing the coating to break into fragments that follow the fracture lines. The size and shape of the released coating fragments are thereby controlled by the preselected dimensions, particularly the width (W) of the texture features.

The following description relates to design parameters to be considered in selecting a surface texture feature for a particular application.

Design Parameters for Texture Features

Design parameters for texture features can generally be categorized as amplitude parameters, spatial parameters or hybrid parameters, although such categorization is intended to be descriptive rather than limiting. Amplitude parameters mainly involve the depth or height (H) of the texture features. Spatial parameters mainly involve the arrangement (e.g., density and proximity) of texture features on the surface of a filament. Hybrid parameters involve both amplitude and spatial parameters. Some parameters may be more important for maximizing the adhesion of a coating to the surface of an implant, whereas other parameters may be more important for controlling the number and/or size of flaked off fragments.

Preferred design parameters for use in designing texture features are listed in Table 1. The Table provides a brief description of each parameter, its common symbol/abbreviation, references or applicable standards in two or three-dimensional space, and default units. The indicated surface roughness parameters can be measured using any appropriate devices and calculation can be made using any appropriate software. An exemplary device is a microscope adapted for use with a Scanning Probe Image Processor (SPIP™), as marketed by Image Metrology A/S (Hørsholm, Denmark). The SPIP™ allows detailed surface characterization using images from electron, interference and optical microscopes. The SPIP™ parameters incorporate the recommendations of the European 8CR Project Scanning tunneling microscopy methods for roughness and micro hardness measurements (Barbato et al. (1995)) and other standards.

TABLE 1

Parameters for selecting texture features

| Symbol | Description | 2-D reference | Default Unit | 3-D reference |
|---|---|---|---|---|
| Amplitude parameters: | | | | |
| Sa | Roughness Average | DIN 4768 ASME B46.1 | nm | ISO/DIS 25178-2; ASME B46.1 |

TABLE 1-continued

Parameters for selecting texture features

| Symbol | Description | 2-D reference | Default Unit | 3-D reference |
|---|---|---|---|---|
| Sq | Root Mean Square (RMS) | ISO 4287/1 ASME 846.1 | nm | ISO/DIS 25178-2; ASME B46.1 |
| Ssk | Surface Skewness | ISO 4287/1 ASME 846.1 | | ISO/DIS 25178-2; ASME B46.1 |
| Sku | Surface Kurtosis | ANSI B.46.1 ASME B46.1 | | ISO/DIS 25178-2; ASME B46.1 |
| Sz | Peak-Peak | ISO 4287/1 | nm | ISO/DIS 25178-2 |
| St | Peak-Peak | ASME B46.1 | nm | ASME B46.1 |
| Sy | Peak-Peak (old SPIP term) | | nm | Stout et al. (1994) |
| Sv | Largest pit height | ASME B46.1 | | ISO/DIS 25178-2; ASME B46.1 |
| Sp | Largest peak height | ASME B46.1 | | ISO/DIS 25178-2; ASME B46.1 |
| Smean | Mean Value | | | |
| Hybrid Parameters | | | | |
| Ssc | Mean Summit Curvature | | 1/nm | Stout et al. (1994) |
| Sdr | Surface Area Ratio | | | ISO/DIS 25178-2 |
| S2A | Projected Area | | nm$^2$ | |
| S3A | Surface Area | | nm$^2$ | |
| Spatial Parameters | | | | |
| Sds | Density of Summits | | 1/μm$^2$ | ASME B46.1; Stout et al. (1994) |
| Std | Texture Direction | | degrees | Stout et al. (1994) |
| Stdi | Texture Direction Index | | | Barbato et al. (1995) |
| Srw | Dominant Radial Wave Length | | nm | Barbato et al. (1995) |
| Str20 | Texture Aspect Ratio at 30% | | | |
| Str37 | Texture Aspect Ratio at 37% | | | |

Most parameters listed in the Table, and described in more detail below, are valid for any rectangular surface feature having the dimensions M×N. However, some parameters, particularly those relating to Fourier transformation, assume that the texture is quadrangular (i.e., M=N).

Some of the parameters depend on the definition of a local minimum and a local maximum. As used herein, a local minimum is defined as a pixel where all eight neighboring pixels are higher, and a local maximum is defined as a pixel where all eight neighboring pixels are lower. Where there are no pixels outside the borders of an image there are no local minimums or local maximums on the borders. In some cases, parameters based on local minimums and/or local maximums may be more sensitive to noise than other parameters.

Prior to making calculations relating to roughness parameters, slope correction is recommended, e.g., using 2nd or 3rd order polynomial plane fit. Scan range and sample density should also be taken into account when reporting roughness data.

Exemplary surface texture parameters can be divided into several categories, which are described in detail, below. The skilled artisan will recognize variations and combinations of these parameters, which, though not specifically described herein, are also included within the scope of the present invention.

Amplitude Parameters

Amplitude is described by six parameters, which provide information about average properties, extremes and shapes of height (H) distribution histograms. The parameters are based on two-dimensional standards that are extended to three dimensions.

Roughness Average (i.e., Sa) is defined as:

$$S_a = \frac{1}{MN} \sum_{k=0}^{M-1} \sum_{l=0}^{N-1} |z(x_k, y_l)| \quad \text{Equation 1}$$

The Root Mean Square (RMS) parameter (i.e., Sq) is defined as:

$$S_q = \sqrt{\frac{1}{MN} \sum_{k=0}^{M-1} \sum_{l=0}^{N-1} [z(x_k, y_l)]^2} \quad \text{Equation 2}$$

Surface Skewness (i.e., Ssk) describes the asymmetry of the height distribution histogram, and is defined as:

$$S_{sk} = \frac{1}{MNS_q^3} \sum_{k=0}^{M-1} \sum_{l=0}^{N-1} [z(x_k, y_l)]^3 \quad \text{Equation 3}$$

A symmetrical height distribution is indicated by Ssk=0, and may be Gaussian like. A surface texture primarily characterized by valleys is indicated by Ssk<0. A surface texture primarily characterized by peaks is indicated by Ssk>0. Values are typically <1 although more extreme surface textures may have values >1 greater than 1.0.

Surface Kurtosis (i.e., Sku) describes the "peakedness" of the surface topography, and is defined as:

$$S_{ku} = \frac{1}{MNS_q^4} \sum_{k=0}^{M-1} \sum_{l=0}^{N-1} [z(x_k, y_l)]^4 \quad \text{Equation 4}$$

Sku values may approaches 3.0 for Gaussian height distributions, while smaller values indicate a broader range of height distributions.

Peak-Peak Height is defined by three parameter (i.e., Sz, St, Sy) according to the indicated ISO and ASME standards and Stout et al. (1994) (Table 1). These parameters relate to the height difference between the highest and lowest pixel in the image.

$$S_z = S_t = S_V = Z_{max} - Z_{min} \qquad \text{Equation 5}$$

Maximum pit height (i.e., Sv) is defined as the largest pit height value.

Maximum peak height (i.e., Sp) is defined as the largest peak height value.

Hybrid Parameters

Three hybrid parameters reflect slope gradients based on local z-slopes.

The Mean Summit Curvature (i.e., Ssc) is the average of the principal curvature of the local maximums on the surface, and is defined as follows for all local maximums where δx and δy are the pixel separation distances:

$$S_{SC} = \frac{-1}{2n} \sum_{i=1}^{n} \left( \left(\frac{\delta^2 z(x,y)}{\delta x^2}\right) + \left(\frac{\delta^2 z(x,y)}{\delta y^2}\right) \right) \qquad \text{Equation 6}$$

The Area Root Mean Square Slope (i.e., Sdq6) is similar to the Sdq but includes more neighbor pixels in the calculation of the slope for each pixel as defined as (Equation 7):

$$S_{dq6} = \frac{1}{(N-6)(M-6)} \sum_{k=3}^{N-3} \sum_{l=3}^{M-3} \Delta^2 |x_k, y_l|$$

$$\Delta^2 |x_k, y_l| = \left( \left\{ \frac{1}{60\Delta x} \begin{bmatrix} -z(x_{k-3}, y_l) + 9z(x_{k-2}, y_l) - 45z(x_{k-1}, y_l) + \\ 45z(x_{k+1}, y_l) - 9z(x_{k+2}, y_l) + z(x_{k+3}, y_l) \end{bmatrix} \right\}^2 + \left\{ \frac{1}{60\Delta y} \begin{bmatrix} -z(x_k, y_{l-3}) + 9z(x_k, y_{l-2}) - 45z(x_k, y_{l-1}) + \\ 45z(x_k, y_{l-1}) - 9z(x_k, y_{l-2}) + z(x_k, y_{l-3}) \end{bmatrix} \right\}^2 \right)^{1/2}$$

The Surfaces Area Ratio (i.e., Sdr) expresses the increment of the interfacial surface area relative to the area of the projected (flat) x-y plane:

$$S_{dr} = \frac{\left(\sum_{k=0}^{m-2} \sum_{l=0}^{x-2} A_{k,l}\right) - (M-1)(N-1)\delta x \delta y}{(M-1)(N-1)\delta x \delta y} 100\% \qquad \text{Equation 8}$$

where Akl is defined as (Equation 9):

$$A_{kl} = \frac{1}{4} \left( \sqrt{\delta y^2 + (z(x_k, y_l) - z(x_k, y_{l+1}))^2} + \sqrt{\delta y^2 + (z(x_{k+1}, y_l) - Z(x_{k+1}, y_{l+1}))^2} \right) \times$$

$$\left( \sqrt{\delta x^2 + (z(x_k, y_l) - z(x_{k+1}, y_l))^2} + \sqrt{\delta x^2 + (z(x_k, y_{l+1}) - z(x_{k+1}, y_{l+1}))^2} \right)$$

For a flat surface, the surface area and the area of the x-y plane are the same and Sdr=0%.

The Projected Area (i.e., S2A) relates to the area of the flat x-y plane as given in the denominator of Equation 7.

The Surface Area (i.e., S3A) expresses the area of the surface area taking the z height into account as given in the numerator of Equation 7.

Spatial Parameters

Spatial properties of surface textures are described by five parameters, namely the density of summits, the texture direction, the dominating wavelength, and two index parameters. The first index parameter is calculated directly from the image, while the other is based on the Fourier spectrum. For these parameters the images must be quadratic.

The Density of Summits, Sds, is the number of local maximums per area:

$$S_{ds} = \frac{NumberoflocalMaximums}{(M-1)(N-1)\delta x \delta y} \qquad \text{Equation 10}$$

The Texture Direction (i.e., Std) is defined as the angle of the dominating texture feature in the image with respect to a dominating structural feature of a particular implant, for example, a filament of a vascular stent. In this manner, if the filaments are arranged perpendicular to the X-scan direction, then Std=O. If the filament is turned clockwise, the angle is positive, and if the filament is turned counter-clockwise, the angle is negative. Note that this parameter is meaningful only if the surface texture has a dominating directional feature.

Std may be calculated from the Fourier spectrum. The relative amplitudes for different angles relating to the filament orientation are calculated by summation of the amplitudes along M equiangularly separated radial lines, as described in Stout et al. (1994). The Fourier spectrum is translated so that the DC component is at (M/2,M/2). An angle α of the i-th line is equal to π/M, where i=0, 1, ..., M−1.

The angular spectrum is calculated by the following formula:

$$A(\alpha) = \sum_{i=1}^{M/2-1} |F(u(M/2 + i\cos(\alpha), v(M/2 + i\sin(\alpha)))| \qquad \text{Equation 11}$$

For non-integer values of p=M/2+i cos(α) and q=M/2+i sin(α), the value of F(u(p),v(q)) is found by linear interpolation between the values of F(u(p),v(q)) in the 2×2 neighboring pixels. The line having the angle a with the highest amplitude sum (i.e., Amax) is the dominating direction in the Fourier transformed image and is perpendicular to the texture direction on the image.

The Texture Direction Index (i.e., Stdi) is a measure of the dominance of the dominating direction, and is defined as the average amplitude sum divided by the amplitude sum of the dominating direction:

$$S_{tdi} = \frac{\sum_{i=0}^{M-1} A(i\pi/M)}{MA_{max}} \qquad \text{Equation 12}$$

The Stdi value is between 0 and 1, where surfaces with a dominant direction have low Stdi values and surfaces lacking a dominant direction have high Stdi values.

The Radial Wavelength (i.e., Srw) is the dominating wavelength found in the radial spectrum calculated by summation of amplitude values around M/(2−1) equidistantly separated semicircles. The radius r of the semicircles (measured in pixels) is in the range r=1, 2, . . . , M/(2−1). The radial spectrum is calculated by the following formula:

$$\beta(r) = \sum_{i=1}^{M-1} |F(u(M/2 + r\cos(i\pi/M), v(M/2 + r\sin(I\pi/M))))| \quad \text{Equation 13}$$

The amplitude for non-integer values of p=M/2+r cos(iπ/M) and q=M/2+r sin(iπ/M) is calculated by linear interpolation between the values of F(u(p),v(q)) in the 2×2 neighboring pixels.

The Dominating Radial Wavelength (i.e., Srw) corresponds to the semicircle with radius, rmax, having the highest amplitude sum, βmax:

$$S_{rw} = \frac{\delta x(M-1)}{r_{max}} \quad \text{Equation 14}$$

The Texture Aspect Ratio Parameters (i.e., Str20 and Str37) are used to identify texture strength (uniformity of texture aspect). It is defined as the ratio of the fastest to slowest decay to correlation 20% and 37% of the autocorrelation function respectively. In principle, the texture aspect ratio has a value between 0 and 1, wherein a surface with a dominant lay has a texture aspect ratio close to 0, while a more spatially isotropic texture feature has a texture aspect ratio closer to 1.

Exemplary Ranges for Selected Parameters

The dimensions of the texture features are preferably selected such that released coating fragments are too small to cause thrombi or emboli. In particular, the dimensions of the texture features are selected such that the width (i.e., side-to-side dimension) of the coating fragments do not exceed about 1 mm (i.e., W is about 1 mm or less). Exemplary values for the maximum width (W) of flaked off coating fragments are from about 0.01 microns (μm) to about 1 mm, and preferably from about 0.1 μm to about 50 μm, from about 5 μm to about 25 μm, or from about 5 μm to about 20 μm. In some cases, the maximum size of the coating fragments is selected to be no greater than the maximum dimensions of naturally occurring particles present at the site of implantation, such as red blood cells. Similarly, the surface area of a texture feature is preferably from about 1 to about 10,000 $\mu m^2$, from about 10 to about 2,500 $\mu m^2$, from about 20 to about 2,000 $\mu m^2$, from about 25 to about 1,500 $\mu m^2$, from about 30 to about 1,000 $\mu m^2$, from about 40 to about 500 $\mu m^2$, or the like.

The height (H) of the texture feature is preferably less than about 50 μm, 30 μm, 25 μm, 20 μm, 15 μm, 10 or even less than about 0.1 μm. Naturally, thinner coatings produce thinner fragments; however, since the thickness of the coating is typically less than the maximum width (W) of the texture feature, W is one of the most important dimensions in terms of controlling the size of coating fragments. The ratio of the thickness of the coating to height (H) is not as critical. The thickness of the coating may be less than H or several times H, depending on, for example, whether the coating covers the peaks of the surface features.

With reference to the foregoing description of surface texture feature design parameters and other parameters that will be apparent to the skilled artisan, Table 2 identifies exemplary ranges of values suitable for designing a surface textured endovascular stent filament having the described features and advantages.

TABLE 2

Exemplary Ranges for Selected Parameters

| Parameters | Units | Exemplary Range |
| --- | --- | --- |
| Roughness Average (Sa) | nm | 200 to 1,100 |
| Root Mean Square (RMS) (Sq) | nm | 300 to 2,400 |
| The Surface Skewness (Ssk) |  | −0.04 to −8.25 |
| Surface Kurtosis (Sku) |  | 2.8 to 53.1 |
| Peak-Peak (Sz, St, Sy) | nm | 2,000 to 19,000 |
| Maximum pit height (Sv) | nm | −1,000 to −16,000 |
| Maximum peak height (Sp) | nm | 700 to 5,300 |
| Mean Summit Curvature (Ssc) | 1/nm | 0.0001 to 0.0013 |
| Surface Area Ratio (Sdr) | % | 12 to 430 |
| Projected Area (S2A) | $nm^2$ | $2.5 \times 10^9$ |
| Surface Area (S3A) | $nm^2$ | 2.5 to $25 \times 10^9$ |
| Density of Summits (Sds) | $1/\mu m^2$ | 0.025 to 0.50 |
| Texture Direction (Std) | deg | 0 to 180 |
| Texture Direction Index (Stdi) |  | 0.576 to 0.895 |
| Dominant Radial Wave Length (Srw) | nm | 13,167 to 53,152 |
| Texture Aspect Ratio at 20% (Str20) |  | 0.08 to 0.94 |
| Texture Aspect Ratio at 37% (Str37) |  | 0.08 to 0.96 |

Advantages of Surface Textured Implants

As discussed in the Background section, previous efforts to address the problem of coatings flaking off a medical implant subject to structural deformation have been aimed at increasing the adhesion of the coating to the surface of the implant. However, under less-than-optimal, real world conditions, the benefit of prior art adhesion improvement is offset resulting in undesirable and uncontrolled coating fragmentation and dislodgment that trigger emboli.

Increasing the adhesion of an elastic coating to the surface of an implant surface may be effective in reducing flaking, particularly where the amount of surface distortion is within the elastic limits of the coating. However, rigid and semi-rigid coatings still have a tendency to break and crack in response to stresses, such as those caused by distortion of the underlying surface structure. The resulting stress fractures propagate producing small coating fragments that can detach from the surface of an implant despite efforts to increase coating adhesion.

The present invention involves surface textures that control the size and shape of coating fragments that detach from the surface of an implant. Controlling the size and shape of coating fragments reduces the risk of embolism, particularly where the implant is in contact with the blood stream, as in the case of a coated stent. In addition to reducing the clinical risk of thrombosis and embolism using conventional coatings, the present invention further enables the use of rigid and semi-rigid coatings that were heretofore unsuitable or undesirable for use as implant coatings due to their tendency to brake and crack. Such coatings include, but are not limited to, poly(d,l-lactic acid), poly(l-lactic acid), poly(d-lactic acid), ethylene vinyl alcohol, ϵ-caprolactone, glycolide, ethylvinyl hydroxylated acetate, polyvinyl alcohol, polyethylene oxides, polyester amides, poly(glycolic acid), polyethylene glycol hyaluronic acid, polyester amide, poly(glycerol-sebacate), cellulose acetate, cellulose nitrate, polyester, polyorthoester, polyanhydride, polyhydroxybutyrate valerate, polycarbonates, tyrosine-derived polycarbonates, and co-polymers and mixtures thereof.

While controlling the size and shape of coating fragments is one aspect of the present invention, another relates to improving the delivery of a therapeutic agent to tissues in contact with or proximal to a coating on the surface of a medical implant. In the case of a vascular stent, the tissue may be the wall of a blood vessel. In the case of an orthopedic implant, the tissue may be bone. With these and other implants, the peaks of the texture features may protrude beyond the coating, or lie just beneath the level of the coating, such that the peaks can contact the tissue either upon implantation, or at some time thereafter, e.g., when some of the coating has eroded or degraded. These peaks may be selected to penetrate cell membranes or layers of cells in a tissue, thereby improving the transport of a therapeutic agent present in the coating due to increased access to the affected tissue.

Figure 9A:
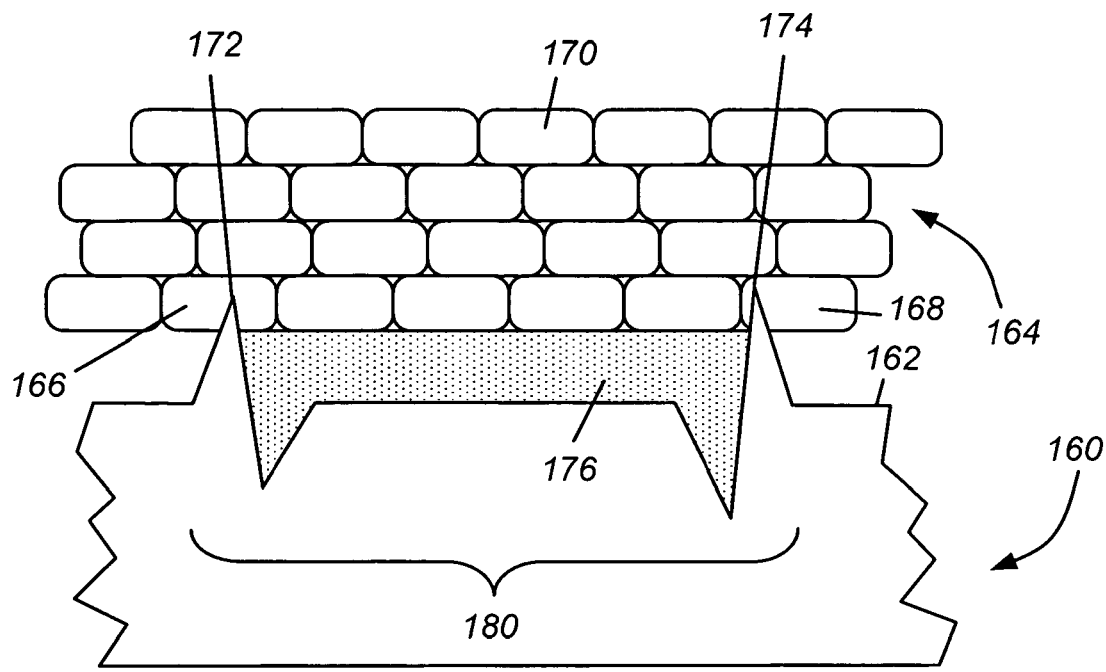
FIG. 9A shows penetration of cell membranes and cells by texture features.

This feature of the present invention is illustrated in FIG. 9A, which shows a first surface 162 of an implant 160 positioned adjacent to a tissue 164 including layers of cells 166, 168, 170. In one embodiment of the invention, the implant may be a stent and the tissue may be the wall of a blood vessel. A peak 172 of a texture feature 180 may penetrate the membrane of a cell 166. Alternatively, a peak 174 of a texture feature 180 may penetrate a cell 168 to contact additional cells or layers of cells within the tissue. Penetrating cell membranes or cells in the tissue adjacent to the implant allows a drug optionally present in a coating 176 to invade the surface layer cell membranes and/or contact cell surfaces deeper within the tissue.

Figure 9B:
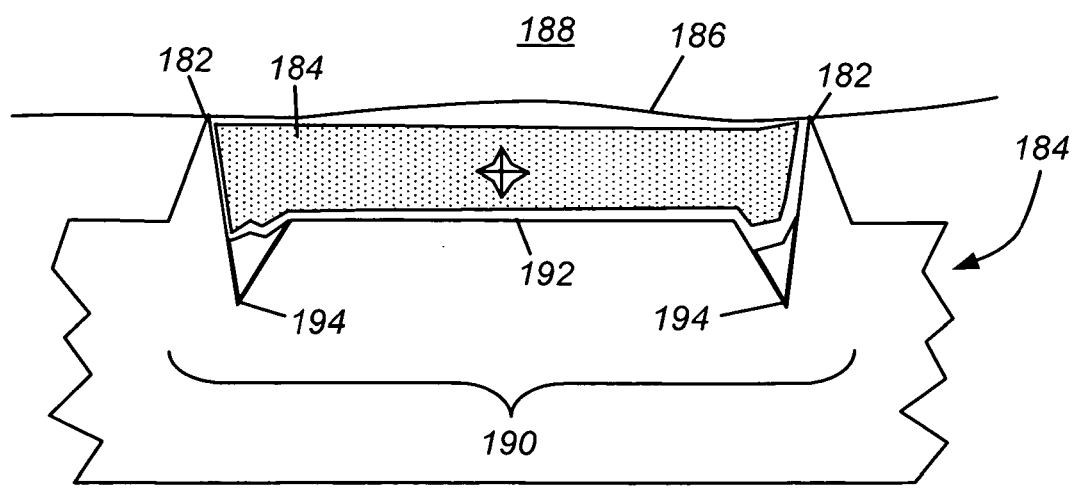
FIG. 9B shows a detached coating fragment held captive against a tissue by texture features.

Yet a further advantage of the present invention is to confine a region or fragments of a coating to a location adjacent to an affected tissue. As illustrated in FIG. 9B, peaks 182 of a texture feature 190 of an implant 184 may prevent a flaked off fragment of coating 184 from leaving the site of implantation, e.g., by holding the fragment captive against the surface 186 of a tissue 188 in the body. While the fragment of coating may no longer be adhered to a plateau 192, peak 182, and/or valley 194 (where present) of the texture feature, and may, therefore, be free to move with respect to the texture feature (indicated by the crossed dotted arrows), the peaks preclude the movement of the coating fragment from its original location adjacent to the surface of the tissue. This feature ensures that a region of tissue adjacent to an implant continues to receive the correct dosage of a beneficial agent present in the coating, even when the corresponding fragment of coating is no longer adhered to the implant.

Yet another advantage of the present invention is an increase in the surface area of the device that is in contact with the coating. In particular, the peaks, valleys and/or plateaus that form the texture features actually increase the surface area of the device. As a result, the coating contacts a larger amount of device surface area, which may provide additional control over coating adhesion, coating fragmentation and dislodgement and, ultimately, drug delivery to the tissue. For example, the actual measured surface area of a stent having texture features may be 1.5 to 10 times greater than the actual measured surface area of a stent without texture features.

The skilled artisan will appreciate these and other features of the present invention, one or more of which may be present in different embodiments.

Coatings and Therapeutic Agents

The coating of the present invention is preferably a rigid or semi-rigid coating, to be distinguished from an elastic coating. While the present invention can be used in combination with an elastic coating, such coatings are generally less prone to cracking and flaking, and, therefore, benefit less from the presence of texture features on the surface of an implant.

As previously described, exemplary rigid or semi-rigid coatings include, but are not limited to, poly(d,l-lactic acid), poly(l-lactic acid), poly(d-lactic acid), a co-polymer of polylactic acid and polyethylene oxide, a co-polymer of polylactic acid and poly(caprolactone), polybutylmethacrylate, polymethyl(meth)acrylate, and other acrylic polymers, polyethylene-co-vinylacetate/polybutylmethacrylate), tyrosine-derived polycarbonates, poly-b-hydroxyalkanoic acids, poly-b-hydroxybutyric acid, polyanhydride, and the like. The coating may be cross-linked or non-cross-linked.

The coating typically includes at least one therapeutically effective agent for delivery to the site of implantation. Exemplary therapeutic agents include, but are not limited to, thrombolytics, antirestenotic agents. vasodilators, antihypertensive agents, antimicrobials, antibiotics, antimitotics, antiproliferatives, antisecretory agents, non-steroidal anti-inflammatory drugs, immunosuppressive agents, growth factors and growth factor antagonists, antitumor and/or chemotherapeutic agents, antipolymerases, antiviral agents, photodynamic therapy agents, antibody targeted therapy agents, antithrombotic agents, dexamethasone, dexamethasone acetate, dexamethasone sodium phosphate, anti-inflammatory steroids, prodrugs, sex hormones, free radical scavengers, antioxidants, biologic agents, radiotherapeutic agents, radiopaque agents, and radiolabelled agents, cytotoxic or cytostatic agents, and the like. Particular, antirestenotic agents include taxol (paclitaxel), doxorubicin, cladribine, colchicines, vinca alkaloids, heparin, hirudin, and their derivatives. In an alternate embodiment, the drug or therapeutic agent may be dispersed in a polymeric coating or covalently integrated into a polymeric coating.

In some embodiments, the coating may be primarily composed of the therapeutic agent, without benefit of an additional support material such as a cross-linked polymer or other structural support. Thus one additional advantage of the invention is the possibility to create implants which do not use polymers as a required element of the therapeutic coating for means of structural support of the therapeutic agent. Polymers coated on the surface of an implant are known to cause undesirable acute and chronic tissue reactions. Undesirable responses can be avoided by reducing the amount of carrier polymer used to deliver a drug, or by or eliminating carrier polymer completely.

A particular class of antirestenotic agents is the macrocyclic trienes, exemplified by rapamycin and other limus drugs, such as sirolimus, everolimus, myolimus, novolimus, pimecrolimus, tacrolimus, and zotarolimus, and the like. Further, a particular limus drug is 40-O-(2-Ethoxyethyl) rapamycin or 42-O-(2-Ethoxyethyl) rapamycin (i.e., BA9™). Macrocyclic triene compounds, and their synthesis, are described, for example, in U.S. Pat. Nos. 4,650,803, 5,288,711, 5,516,781, 5,665,772, 6,153,252, and 6,273,913, PCT Publication No. WO 97/35575, and U.S. Patent Application Nos. 2000021217, 2001002935, 20080097591, 20080097568, and 20050211680, each of which is incorporated by reference herein.

Because the present invention may increase adhesion of a coating to the surface of an implant, underlayers or primers are not required but may be used without defeating the purpose of the invention. Exemplary undercoat materials include, but are not limited to, poly(d,l-lactic acid), poly(l-lactic acid), poly(d-lactic acid), ethylene vinyl alcohol, s-caprolactone, ethylvinyl hydroxylated acetate, polyvinyl alcohol, polyethylene oxides, poly(dichloro-para-xylylene), silane-based coatings including organosilanes, aminosilane, vinyl silane, epoxy silane, methacryl silanes, alkylsilane, phenyl silane, and chlorosilane, polytetrafluoroethylene (TEFLON®) and other fluoropolymers, and co-polymers thereof and mixtures thereof. The underlayer can be deposited from a solvent-based solution, by plasma-coating, or by other coating or deposition processes (see, e.g., U.S. Pat. No. 6,299,604). The underlayer typically has a thickness of between about 0.5 micron and 5 microns, and should take up less than 20%, less than 15%, or even less than 10% of the volume in a texture feature.

Manufacturing Process

Another aspect of the present invention is a manufacturing process for producing a surface textured implant. The process involves removing and/or redistributing material on the surface of an implant to produce one or more texturing features for controlling the size and shape of pieces of coating that flake off the surface of the implant. The surface texture can be created by technologies such as chemical etching, photolithography, micro/nano-abrasion, laser engraving, die transfer printing, water jet cutting, electro-pitting gas plasma etching, corona process, and other chemical-mechanical, chemical-photo, chemical-electrical, and electrical-mechanical techniques.

Valleys (i.e., depressions relative to the surface) in a texture feature are typically created by removing material but can be created by forming or extrusion. Peaks may be created by adding material to the surface of an implant or by forming or extrusion, wherein the material that forms the peaks originates from another (typically adjacent) location on the surface of the implant.

The present invention is not limited to a particular implant material, and can utilize many materials commonly used for making implants and medical devices. Exemplary materials include, but are not limited to, metals, polymers, and ceramics. Metals further include, but are not limited to, stainless steel, cobalt chromium, nitinol, inconel, molybdenum, platinum, titanium, tantalum, tungsten, gold, platinum, iridium, and other medical grade metals. Polymers further include, but are not limited to, poly(d,l-lactic acid), poly(l-lactic acid), poly(d-lactic acid), methacrylate polymers, such as polybutyl methacrylate, polymethyl(meth)acrylate, and the like, ethylene vinyl alcohol, ε-caprolactone, glycolide, ethylvinyl hydroxylated acetate, polyvinyl alcohol, polyethylene oxides, polyester amides, poly(glycolic acid), polyethylene glycol hyaluronic acid, polyester amide, poly(glycerol-sebacate), nanoscale structures of carbon, acetal copolymer, acetal homopolymer, acrylonitrile butadiene styrene, polycarbonate, nylon, polyamide, polyacrylate, polyaryl sulfone, polycarbonate, polyetherketone, polyetherimide, polyether sulfone, polyethylene terephthalate, polyimide, polyphenylene oxide, polyphenylene sulfide, polypropylene, polysulfone, polyurethane, polyvinyl chloride, styrene acrylonitrile, carbon or carbon fiber; cellulose acetate, cellulose nitrate, silicone, polyethylene teraphthalate, polyurethane, polyamide, polyester, polyorthoester, polyanhydride, high molecular weight polyethylene, polytetrafluoroethylene, polyanhydride, polyhydroxybutyrate valerate, co-polymers and mixtures thereof, and other polymers suitable for use in making implants. Ceramic materials further include, but are not limited to, hydroxyapatite, zirconia ceramics, and pyrocarbon ceramic-like materials.

The foregoing description and examples are intended to be illustrative and not limiting. Other features and embodiments of the present devices and methods will be apparent in view of the disclosure.

What is claimed is:

1. A radially expandable device for introducing into the body tissues of a subject to produce a beneficial effect, said device comprising:
    an upper surface able to contact tissue at a treatment site of the body; wherein said upper surface comprises a coating and a plurality of texture features designed to interact with said coating and cause fragments of said coating to flake off said upper surface as a result of radial expansion of said device at said treatment site wherein the texture features comprise stress risers that have peak-peak height (Sz) values of between 2000 to 19000 nanometers and that define discrete surface regions and control the size and the shape of the fragments and wherein the maximum width of the discrete surface regions are from 0.1 µm to 50 µm.

2. The device of claim 1 wherein said texture features control the quantity of said fragments.

3. The device of claim 1 wherein said texture features comprise one or more peaks.

4. The device of claim 1 wherein said texture features comprise one or more valleys.

5. The device of claim 1 wherein said texture features comprise one or more peaks and valleys.

6. The device of claim 1 wherein said stress risers control the size and the shape of the fragments by the initiation and propagation of stress fractures in said coating.

7. The device of claim 1 wherein said texture features comprise one or more plateaus.

8. The device of claim 1 wherein said texture features comprise one or more peaks, valleys and plateaus.

9. The device of claim 1 wherein said fragments are too small to cause thrombi.

10. The device of claim 1 wherein said fragments are too small to cause emboli.

11. The device of claim 1 wherein the Roughness Average (Sa) is between 200 and 1,100 nm.

* * * * *